United States Patent
Wahlstrom et al.

(10) Patent No.: US 7,212,869 B2
(45) Date of Patent: May 1, 2007

(54) LEAD RETENTION MEANS

(75) Inventors: Dale A. Wahlstrom, Plymouth, MN (US); Jay A. Erlebacher, Tenafly, NJ (US); John L. Sommer, Coon Rapids, MN (US); Mark T. Stewart, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 164 days.

(21) Appl. No.: 10/771,643

(22) Filed: Feb. 4, 2004

(65) Prior Publication Data

US 2005/0182472 A1    Aug. 18, 2005

(51) Int. Cl.
*A61N 1/00* (2006.01)
(52) U.S. Cl. ..................................... 607/126
(58) Field of Classification Search ........ 607/126–128, 607/116; 604/175
See application file for complete search history.

(56) References Cited

U.S. PATENT DOCUMENTS

| | | | |
|---|---|---|---|
| 3,939,843 A | 2/1976 | Smyth ........................ 128/404 |
| 4,272,577 A | 6/1981 | Lyng | |
| 4,419,819 A | 12/1983 | Dickhudt et al. ............. 29/857 |
| 4,540,195 A | 9/1985 | Smith-Johannsen | |
| 4,796,643 A | 1/1989 | Nakazawa et al. .......... 128/785 |
| 4,827,940 A | 5/1989 | Mayer et al. | |
| 4,841,971 A | 6/1989 | Hess | |
| 4,876,109 A | 10/1989 | Mayer et al. | |
| 4,957,118 A | 9/1990 | Erlebacher ................... 128/785 |
| 5,011,494 A | 4/1991 | von Recum et al. | |
| 5,219,361 A | 6/1993 | von Recum et al. | |
| 5,425,362 A * | 6/1995 | Siker et al. .................. 600/376 |
| 5,531,781 A * | 7/1996 | Alferness et al. ........... 607/122 |
| 5,545,206 A * | 8/1996 | Carson ........................ 607/126 |
| 5,580,699 A | 12/1996 | Layman et al. | |
| 5,653,690 A * | 8/1997 | Booth et al. ............ 604/103.07 |
| 5,733,322 A | 3/1998 | Starkebaum | |
| 5,865,843 A | 2/1999 | Baudino | |
| 5,911,733 A * | 6/1999 | Parodi ........................ 623/1.15 |
| 5,984,896 A * | 11/1999 | Boyd ........................... 604/175 |
| 5,999,858 A | 12/1999 | Sommer et al. | |
| 6,006,122 A | 12/1999 | Smits .......................... 600/373 |
| 6,144,882 A | 11/2000 | Sommer et al. | |
| 6,240,322 B1 * | 5/2001 | Peterfeso et al. ........... 607/126 |
| 6,263,249 B1 | 7/2001 | Stewart et al. | |
| 6,293,907 B1 * | 9/2001 | Axon et al. .................. 600/114 |
| 6,304,786 B1 | 10/2001 | Heil, Jr. et al. ............. 607/126 |
| 6,511,452 B1 * | 1/2003 | Rejai et al. .................... 604/15 |
| 6,549,811 B2 | 4/2003 | Stewart et al. | |
| 6,594,515 B2 * | 7/2003 | Watson ........................ 600/376 |
| 6,599,310 B2 * | 7/2003 | Leung et al. ................ 606/228 |

(Continued)

OTHER PUBLICATIONS http://www.amonline.net.au/fishes/students/scales, "Fish Scales," Australian Museum online, p. 1-2 (1998-2001).

(Continued)

*Primary Examiner*—Mark Bockelman
(74) *Attorney, Agent, or Firm*—Michael C. Soldner; Girma Wolde-Michael (57) ABSTRACT

A medical device having retention means extending along a length of an elongate body of the medical device including a plurality of projections adapted to interfere with a wall of a generally tubular vessel to retain the body within the vessel.

38 Claims, 9 Drawing Sheets

U.S. PATENT DOCUMENTS

| | | | |
|---|---|---|---|
| 6,767,339 B2 * | 7/2004 | Reydel | 604/175 |
| 6,842,648 B2 * | 1/2005 | Partridge et al. | 607/126 |
| 6,846,296 B1 * | 1/2005 | Milbocker et al. | 601/153 |
| 2001/0041874 A1 * | 11/2001 | Reydel | 604/266 |
| 2001/0044646 A1 * | 11/2001 | Marshall et al. | 607/127 |
| 2003/0199961 A1 | 10/2003 | Bjorklund et al. | 607/126 |
| 2004/0230282 A1 * | 11/2004 | Cates et al. | 607/126 |
| 2004/0243210 A1 * | 12/2004 | Morgan et al. | 607/122 |

OTHER PUBLICATIONS

Product sheet, Biotronik, http://www.biotronik.com/content/detail.php?id=349 (2001).

Product sheet, Guidant Corporation, http://www.guidant.com/products/producttemplates/crm/easytrak.shtml#Nominal%20Specifications (2004).

* cited by examiner

LEAD RETENTION MEANS

TECHNICAL FIELD

The present invention relates to medical devices and more particularly to means for retaining or preventing dislodgement of a lead positioned within a body.

BACKGROUND

Medical devices often include a therapy generator and one or more elongate leads, coupled thereto, which are positioned within a patient's body to deliver therapy from the generator. Such therapy may be in the form of electrical stimulation, delivered via electrical conductors extending through a lead body, or fluid infusion, delivered via a lumen extending through a lead body. Some examples of electrical stimulation include pacing and defibrillation; some examples of fluids, which may be infused, include drugs, nutrients, and genetic materials. In many applications, leads are inserted through one or more blood vessels and are ultimately positioned within a blood vessel where the lead must be retained for a period of time in order to deliver the therapy. Therefore it is desirable to provide lead retention means allowing insertion or forward motion of lead, to position the lead within a vessel, while preventing retraction or rearward motion of the lead during therapy delivery.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
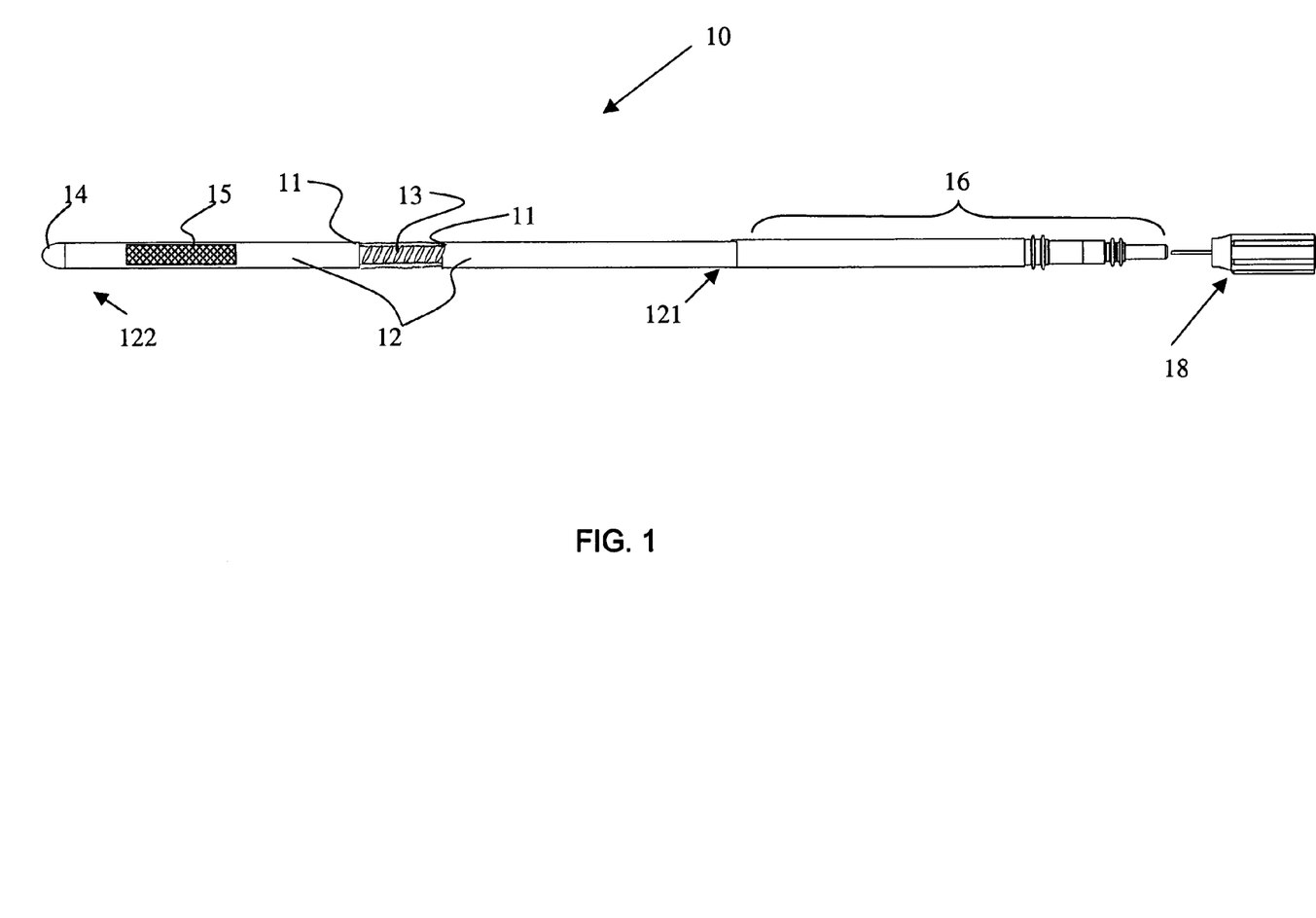
FIG. 1 is a plan view with a partial section of a lead including means for retention according to one embodiment of the present invention.

FIG. 1 is a plan view with a partial section of a lead 10 including means for retention 15 according to one embodiment of the present invention. FIG. 1 illustrates lead 10 including a lead body 12, a connector 16 coupled to a proximal end 121 of the lead body 12 and an electrode 14 coupled to a distal end 122 of the lead body 12; a conductor 13, extending within an outer sheath 11, couples electrode 14 to connector 16, in order to deliver electrical stimulation, and forms a lumen for slideably engaging a stylet 18. Means and materials for constructing such a lead are well known to those skilled in the art.

Figure 6:
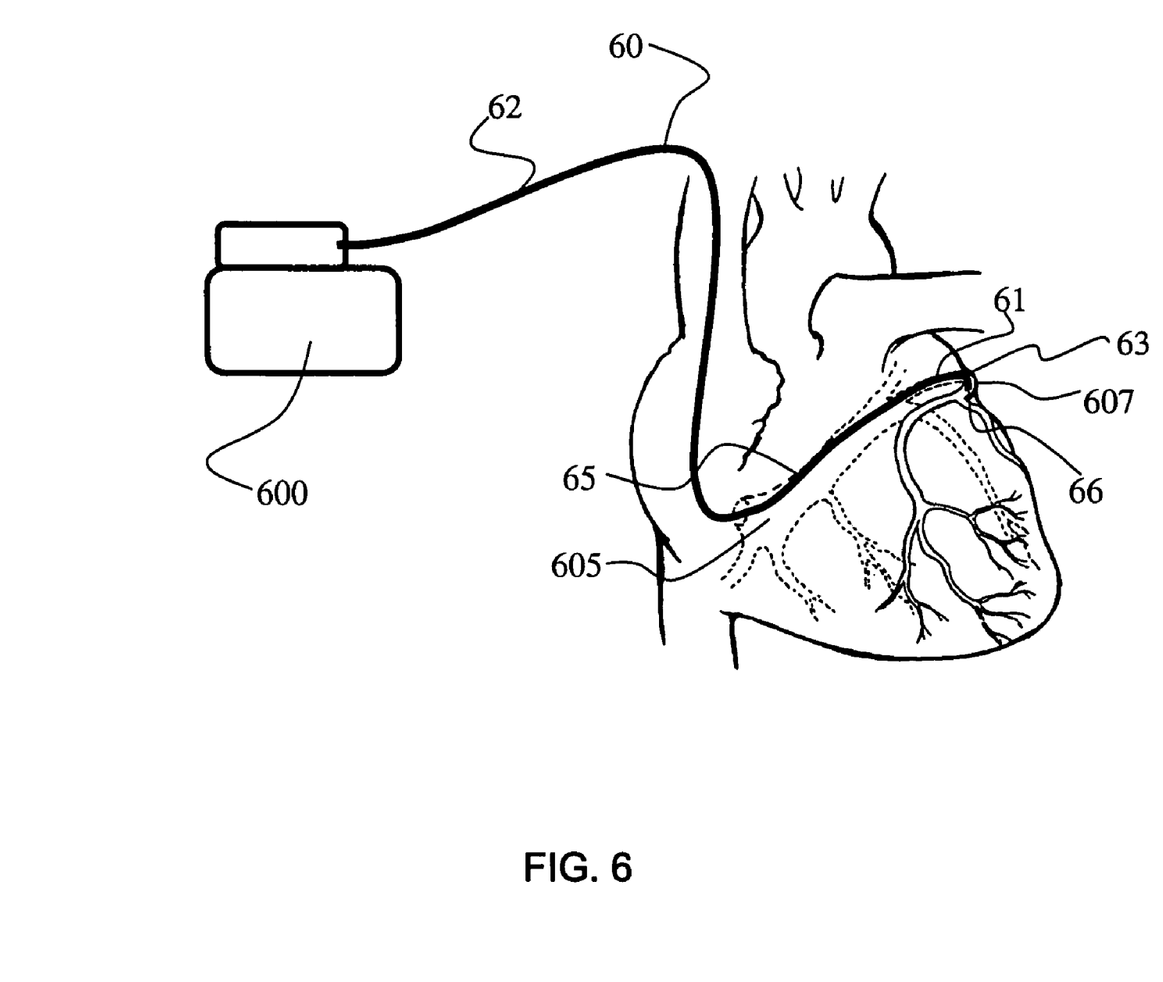
FIG. 6 is a schematic view of a medical device, which may incorporate retention means according to embodiments of the present invention.

FIG. 1 further illustrates retention means 15 formed along an outer surface of lead body 12 in proximity to distal end 122. According to embodiments of the present invention, retention means 15 allows insertion of lead body 12 through a vessel, for example a vessel 607 as illustrated in FIG. 6, while preventing retraction of lead body 12 within the vessel due to an interference of retention means 15 along a wall of the vessel that contacts lead body 12. Retention means according to some embodiments of the present invention extends along a length greater than or equal to approximately 1 mm and may be implemented along any portion of a lead body alone or in conjunction with other retention means; further, retention means 15 may be an integral part of outer sheath 11 or may be formed on a separate collar fitted about lead body 12, either in-line with or about outer sheath 11. Suitable materials for outer sheath 11 and retention means 15 include those that are biocompatible, examples of which include, but are not limited to, silicone and polyurethane.

Figure 2A:
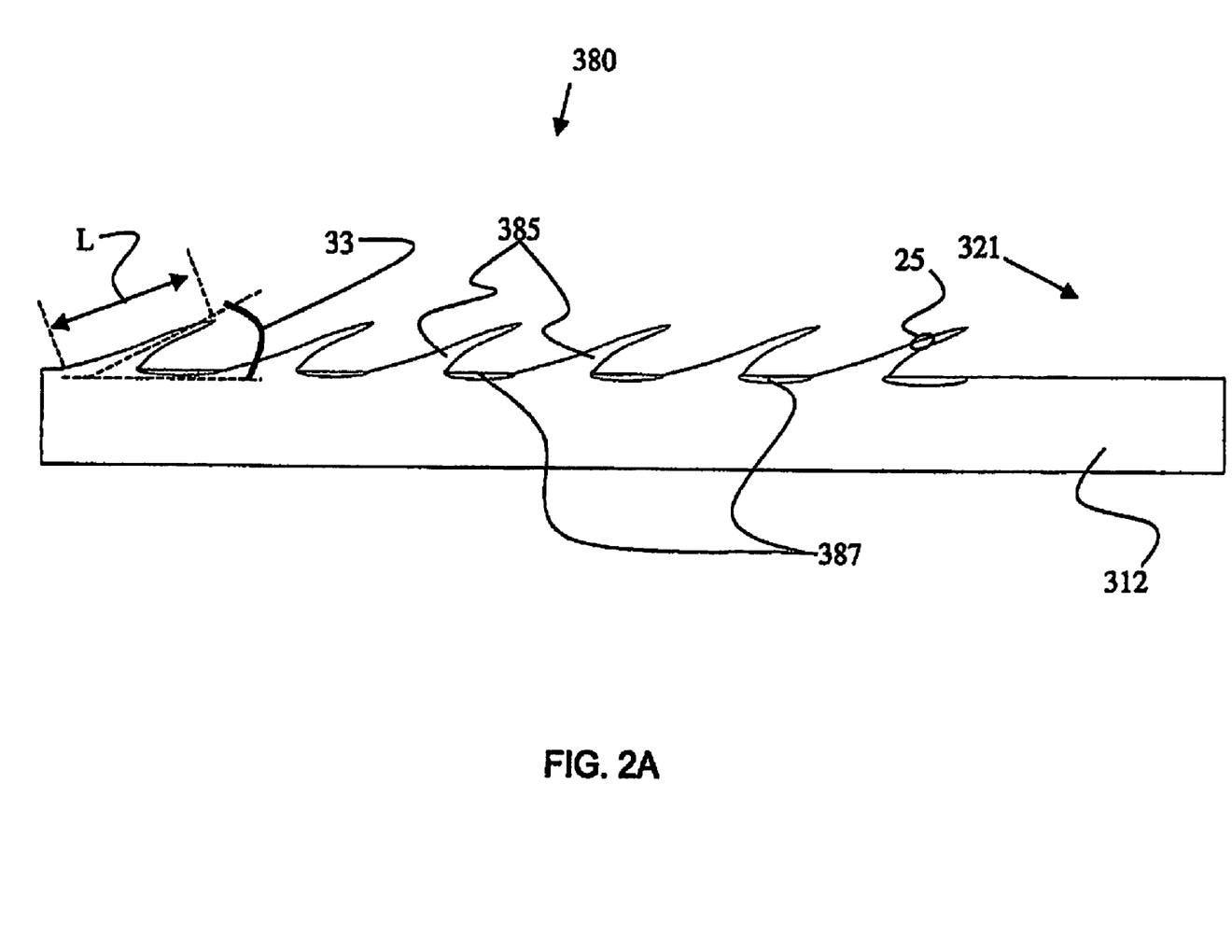
FIG. 2A is an enlarged plan view of a retention means according to one embodiment of the present invention.
Figure 2B:
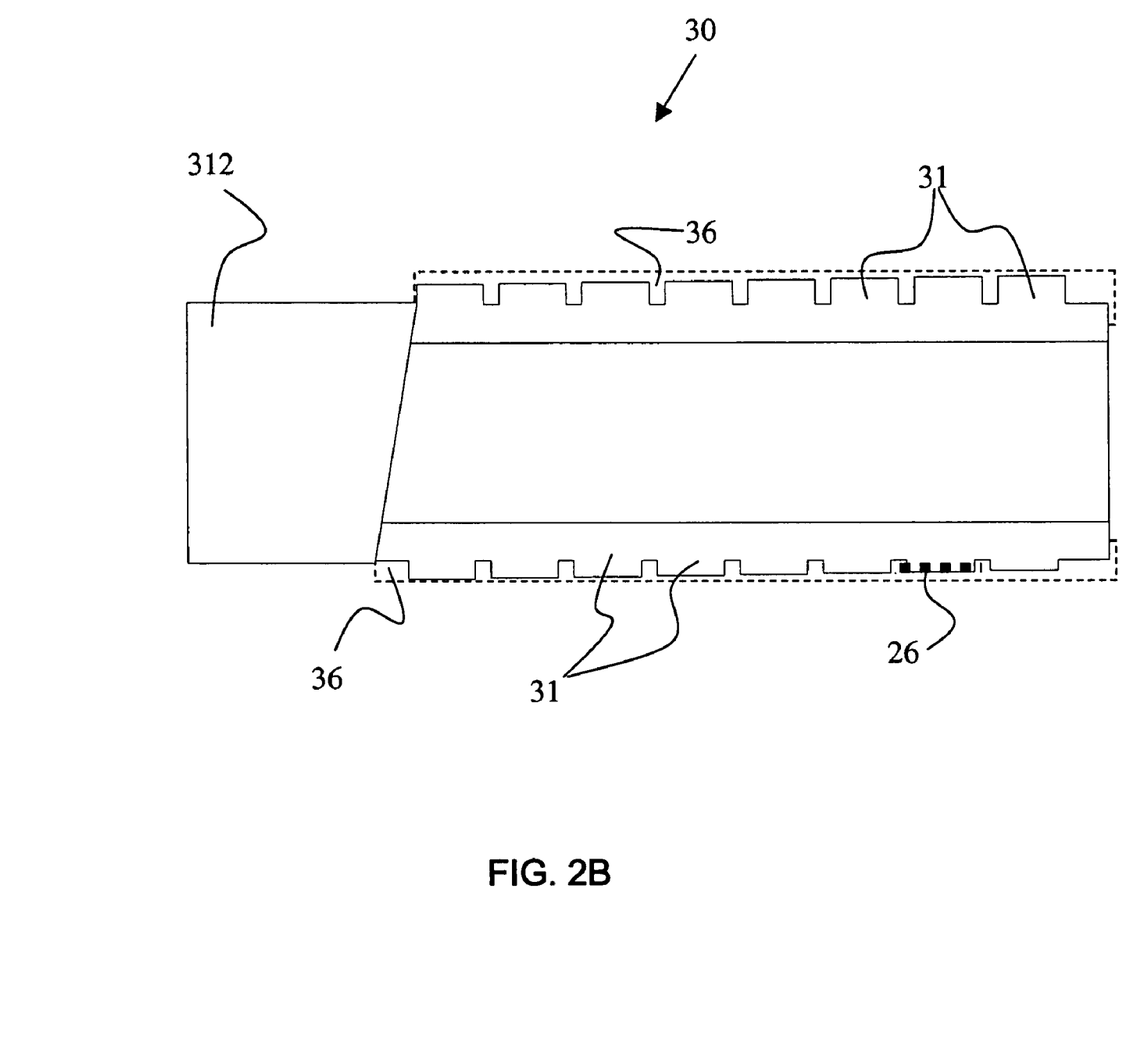
FIG. 2B is an enlarged partial section view of means for retention according to an alternate embodiment.
Figure 2C:
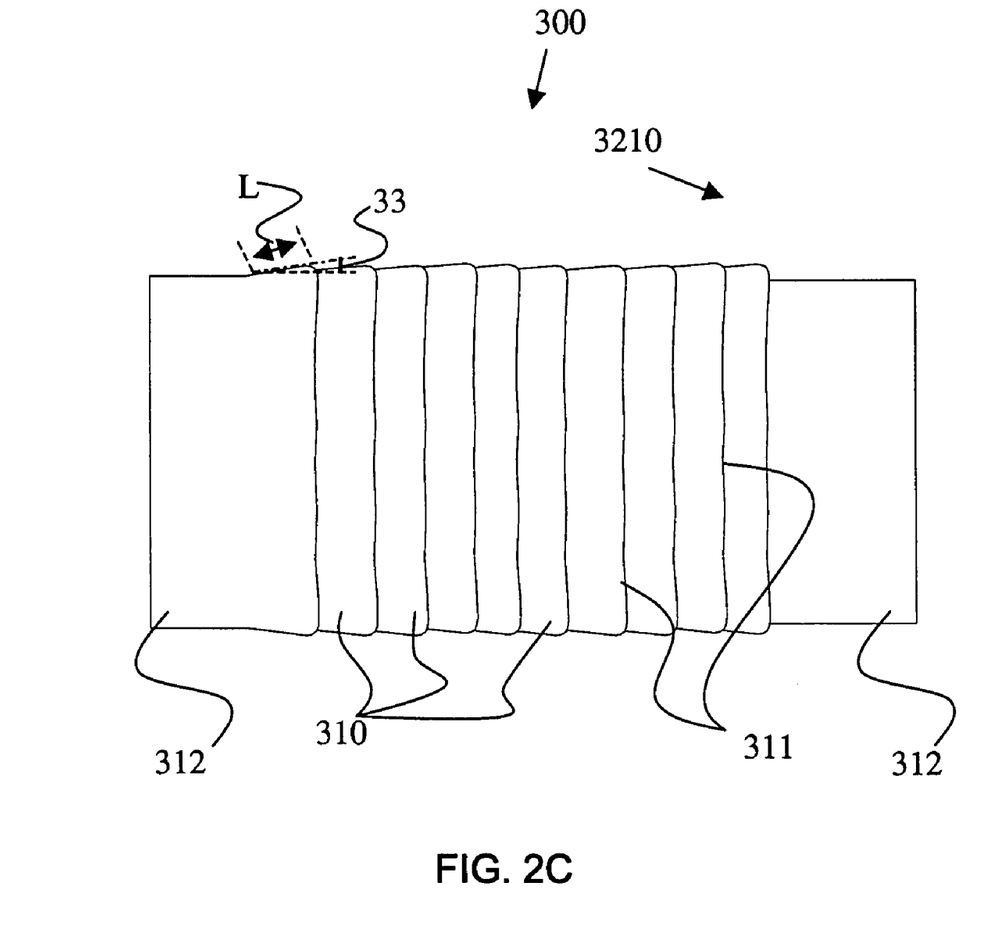
FIG. 2C is an enlarged plan view of means for retention according to another embodiment.
Figure 2D:
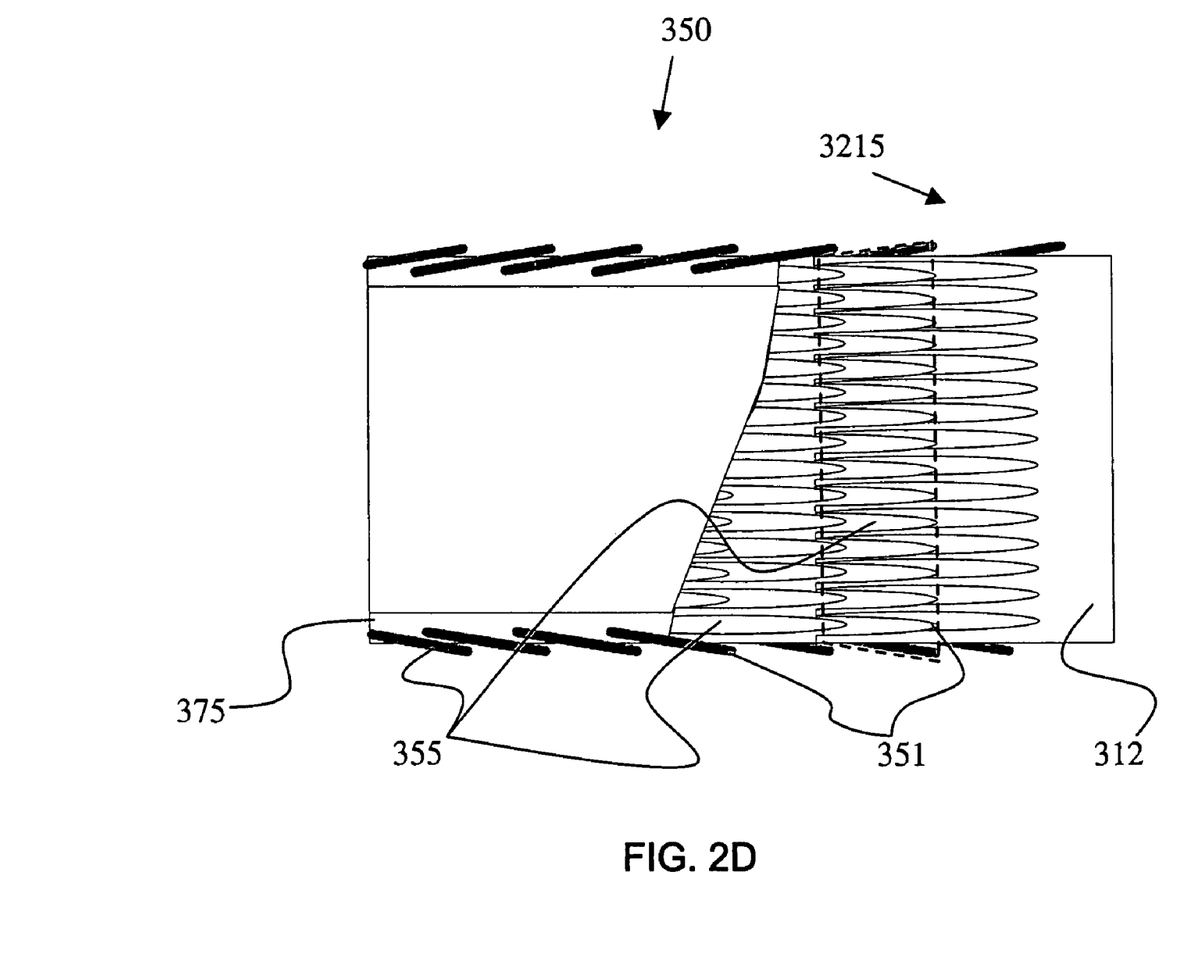
FIG. 2D is an enlarged partial section view of means for retention according to yet another embodiment of the present invention.

Various embodiments of retention means include projections formed along retaining segments as illustrated in FIGS. 2A–D and 4A–5B. It should be noted that alternate embodiments include, but are not limited to, retaining segments extending around an entire circumference of a lead body and segments extending only about a portion of the circumference of the lead body. For example, a plurality of projections may lie in a line, single file, along a length of a retaining segment, as illustrated in FIG. 2A, or each individual projection may extend circumferentially about all or a portion of a retaining segment, as illustrated in FIG. 2C, or a plurality of projections may lie approximately side-by-side about all or a portion of a circumference, as illustrated in FIG. 2D.

In some embodiments, retaining segments as a whole or just the projections may be formed of a bioadsorbable material, examples of which include those taught in lines 10–24 of U.S. Pat. No. 6,173,206. According to these embodiments, if a lead body is chronically implanted, the retaining segment or projections would remain intact long enough to hold the body in place for a period of time up to tissue encapsulation of the body; this may facilitate extraction of a chronically implanted lead. One example of an appropriate bioadsorbable material, polydioxanone is described along with means for molding the material in U.S. Pat. No. 4,490,326, the teachings of which are incorporated by reference herein.

FIG. 2A is an enlarged plan view of means for retention according to one embodiment of the present invention. FIG. 2A illustrates a retaining segment 380 including a plurality of barb-like projections 385 positioned in a single-file line along a length of the segment 380; each of the plurality of projections 385 include a length L and extend laterally from a lead body 312 toward a proximal end 321 at an angle 33, which, according to some embodiments, is less than approximately 45 degrees. According to this embodiment of the present invention and various other embodiments illustrated herein length L is greater than approximately 100 microns. FIG. 2A further illustrates projections 385 as portions of a wall 387 forming retaining segment, having been lifted out of wall 387 according to one embodiment of the present invention. FIG. 2B illustrates an alternate retaining segment 30 extending along a length of lead body 312 and including tread-like projections 31 extending laterally from lead body 312 to form a textured surface adapted to engage a vessel wall, similar to, for example, a sole of a shoe designed to facilitate traction. According to some embodiments of the present invention, projections, i.e. 385, 31, are directly formed in outer surfaces, being integral with a bulk material underlying the surfaces, but, according to alternate embodiments, the projections are formed of separate materials either embedded in or adhered to these surfaces. Alternative methods of forming examples of these embodiments will be described herein below.

FIG. 2B further illustrates retaining segment 30 including a coating 36, which is soluble in body fluids; according to this embodiment, coating 36 fills in around projections 31 and remains intact temporarily, during positioning of lead body 312, so that lead body 312 may be moved back and forth through a vessel if repositioning is necessary. Suitable materials forming coating 36 are soluble in body fluids (within a temperature range encompassing normal body temperature), non-toxic, biocompatible and non-pyrogenic; examples of such a material include sugar derivatives, such as mannitol and dextrose, salts, such as sodium chloride and potassium chloride, and polyvinylpyrrolidone (PVP). Portions of U.S. Pat. No. 4,827,940 teaching methods for forming and applying a mannitol solution are incorporated by reference herein. According to an alternate embodiment, a covering in the form of a thin wall tube may be deployed over retaining segment 30 in place of coating 36. It should be noted that any of the embodiments described herein may include such a coating or a covering facilitating positioning of lead bodies.

FIG. 2C is an enlarged plan view of means for retention according to another embodiment. FIG. 2C illustrates a retaining segment 300 coupled to a portion of lead body 312 and including a proximal end 3210 and a plurality of projections 310, each of which extend around all or a portion of a circumference of lead body 312 and extend laterally from lead body 312 at angle 33 with terminal ends 311 of projections 310 directed toward proximal end 3210.

FIG. 2D is an enlarged partial section view of means for retention according to yet another embodiment of the present invention. FIG. 2D illustrates a retaining segment 350 including a plurality of fish scale-like projections 355 positioned side-by-side about a circumference of lead body 312 and along a length of segment 350 and including terminal ends 351 directed toward a proximal end 3215. FIG. 2D further illustrates projections 355 as discrete elements embedded in an underlying surface 375 of segment 350 according to one embodiment of the present invention. FIG. 2D also illustrates, by way of a dashed line connecting projections 355 around a circumference, another embodiment in which embedded elements forming projections may be rings or portions of a coil circling a portion of or the entire circumference of segment 350 creating projections similar to projections 310 illustrated in FIG. 2C.

According to further alternate embodiments, some or all projections of a retaining segment, for example projections 385, 31, 310 and 355 (FIGS. 2A–D), each include micro-features further enhancing engagement of the projections with the vessel wall. In FIG. 2A such a feature is illustrated on one of projections 385 as a hole or indentation 25; in FIG. 2B such a feature is illustrated as a modified surface 26 on one of projections 31 wherein surface 26 includes texture, adhesive spots, or some material promoting thrombotic adhesion to vessel wall.

Methods for forming various embodiments of retaining segments, for example those depicted in FIGS. 2A–D, include, but are not limited to, molding, extrusion, cutting, laser ablation, and coating. These methods may form projections directly in outer surfaces, such that they are integral with a bulk material underlying the surfaces, or may integrate the projections with the surface by embedding or adhering.

According to some embodiments of the present invention, transfer or injection molding, using methods known to those skilled in the art, are used to form a retaining segment including projections, examples of which include those depicted in FIGS. 2B–C. According to other embodiments, a cutting process may be used to create projections on a retaining segment, for example segment 380 illustrated in FIG. 2A; a blade may be used to nick the surface or to cut all the way through a wall of the retaining segment.

Alternatively, laser ablation may be used to create projections from a bulk material of a retaining segment, i.e. FIGS. 2B–C, or by exposing, at a surface of the segment, portions of materials which have been embedded within the bulk material underlying the surface during, for example, a molding or extrusion process, i.e. FIG. 2D. U.S. Pat. No. 5,580,699 describes a suitable laser ablation process, which may be used to form retaining segments and the pertinent teachings of the '699 patent are incorporated by reference herein. U.S. Pat. No. 4,272,577 describes an extrusion process for forming ski bases having direction-dependent friction coefficients wherein harder particles, within a plastic matrix flowing through a slit nozzle, become obliquely oriented relative to the surface of the base; in one case, by means of a temperature gradient across the nozzle. We contemplate that similar methods may be developed by those skilled in the art, according to the teachings of the '577 patent, in order to extrude retaining segments according to the present invention, and incorporate by reference the pertinent teachings of the '577 patent herein. Some composite materials suitable for embodiments of the present invention include but are not limited to polyamide and polyimide particles, polyester fibers, carbon fibers or particles and any combination thereof blended with silicone.

According to further alternate embodiments a coating applied to a surface of a retaining segment may form projections and or micro-features on projections, for example similar to those illustrated in FIGS. 2B–C. Stewart et al. describe an example of a suitable coating process via plasma deposition in commonly assigned U.S. Pat. No. 6,549,811, which is incorporated by reference in its entirety herein. Furthermore coatings including particles blended within, for example a silicone medical adhesive including biocompatible metal particles or hard plastic particles may form an embodiment of the present invention for example similar to those illustrated in FIGS. 2B and 2D.

Figure 3:
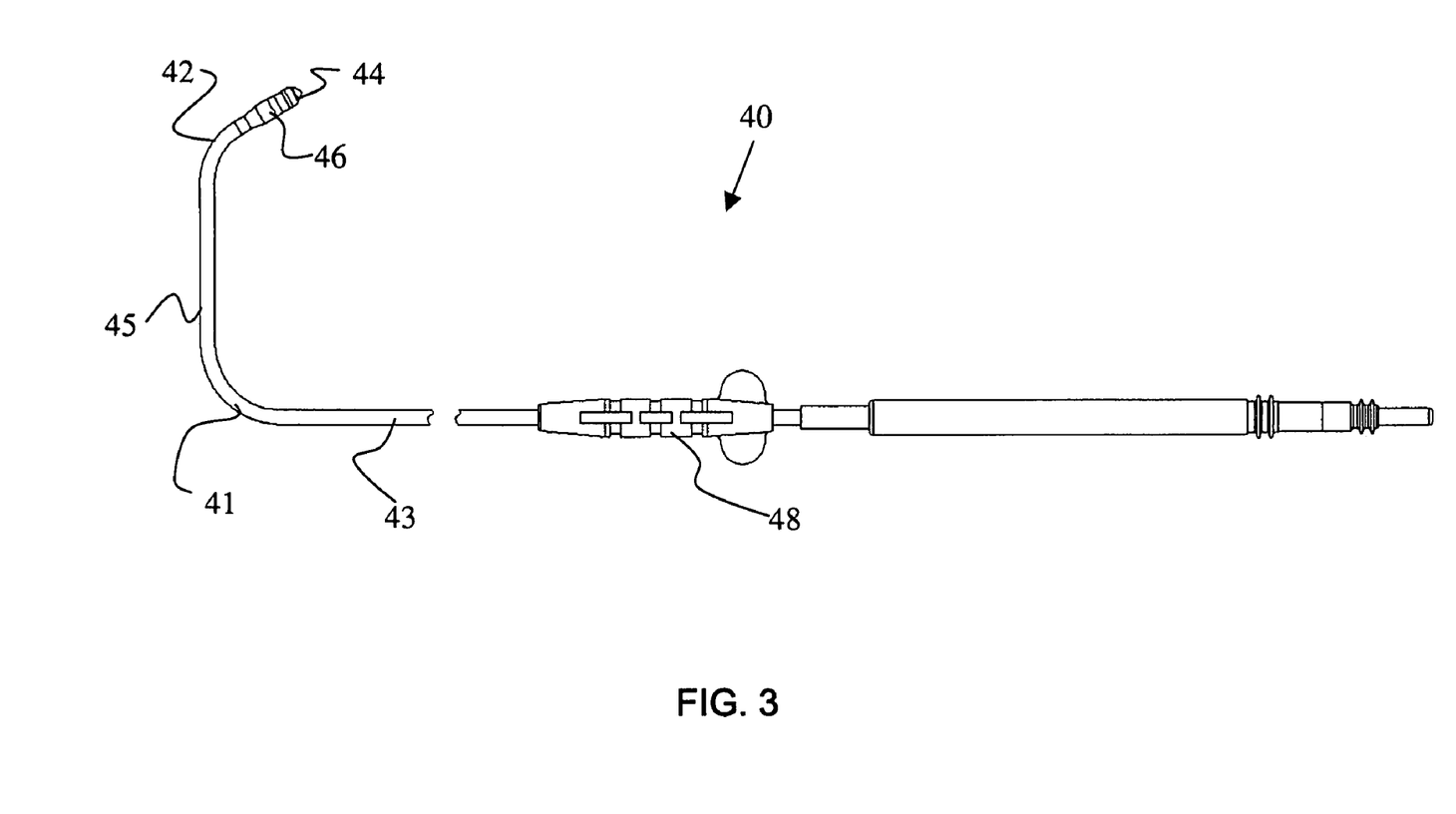
FIG. 3 is a plan view of a lead which may incorporate retention means according to embodiments of the present invention.

FIG. 3 is a plan view of a lead 40, which may incorporate retention means according to embodiments of the present invention. FIG. 3 illustrates lead 40 including a proximal portion 43, a first preformed bend 41 extending from proximal portion 43 to an intermediate segment 45 and a second preformed bend 42 extending from intermediate segment 45 to distal segment 46, which is terminated by a tip 44. Such a lead is fully described in commonly assigned U.S. Pat. No. 5,999,858, which is herein incorporated by reference in its entirety. According to embodiments of the present invention, first and second bends 41 and 42 acting as means for retention of lead body in a coronary vessel, for example a coronary sinus 605 or a branch vessel 607 thereof illustrated in FIG. 6, are supplemented by any of the retaining segments described herein, which may be formed along the lead body surface at first bend 41, intermediate segment 45, second bend 42, distal segment 46, or any combination thereof. Any other combination of bends within a lead body is within the scope of the present invention.

Figure 4A:
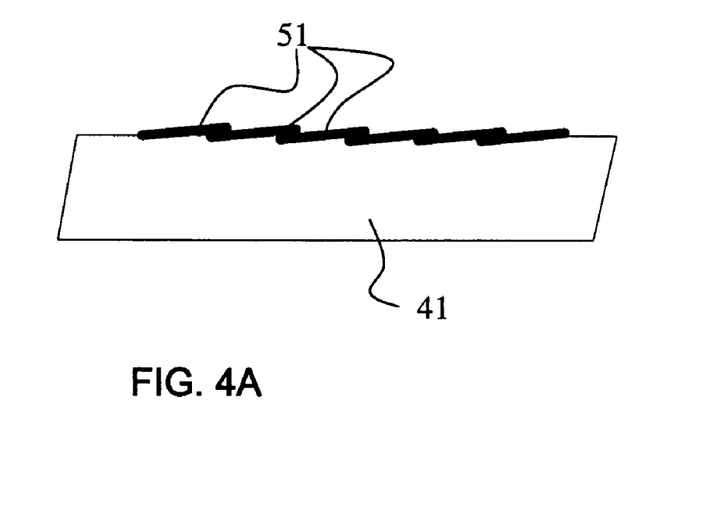
FIGS. 4A–B are plan views of a portion of a lead body including retention means according to an alternate embodiment of the present invention.
Figure 4B:
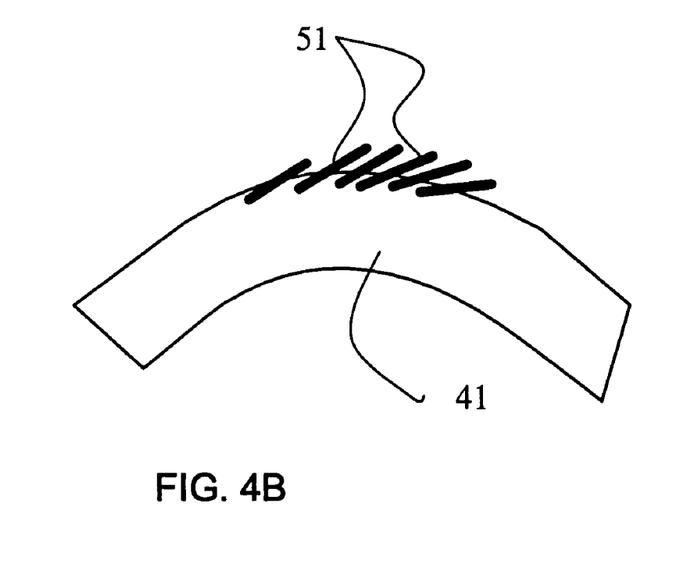

FIGS. 4A–B are partial plan views of one embodiment of lead 40 showing only a portion at first bend 41, which includes a retaining segment formed by projections 51. According to some embodiments of the present invention a retaining segment may be activated by a bending of a lead body as illustrated in FIGS. 4A–B. If a stylet, for example stylet 18 shown in FIG. 1, is inserted into lead 40 to straighten preformed bend 41, projections 51 become approximately parallel with an outer surface of lead 40, as illustrated in FIG. 4A. Once the stylet is removed preformed bend 41 reforms such that projections 51 protrude laterally and are thus activated to prevent rearward motion of lead 40 within a vessel. If it becomes necessary to reposition lead 40, the stylet may be reinserted to straighten bend 41 thus bringing projections into approximate alignment with the surface of lead 40. It should be noted that the embodiment illustrated in FIG. 2D may be of the type illustrated in FIGS. 4A–B.

FIG. 3 further illustrates lead 40 including an anchoring sleeve 48 positioned about proximal portion 43 thereof. According to an additional embodiment of the present invention, means for retention as illustrated herein, may be formed along an outer surface of proximal portion to provide frictional forces complementing anchoring sleeve 48 at a venous entry point. The means for retention may either engage an inner surface of anchoring sleeve 48 or engage a vein wall in proximity to the entry point.

Figure 5A:
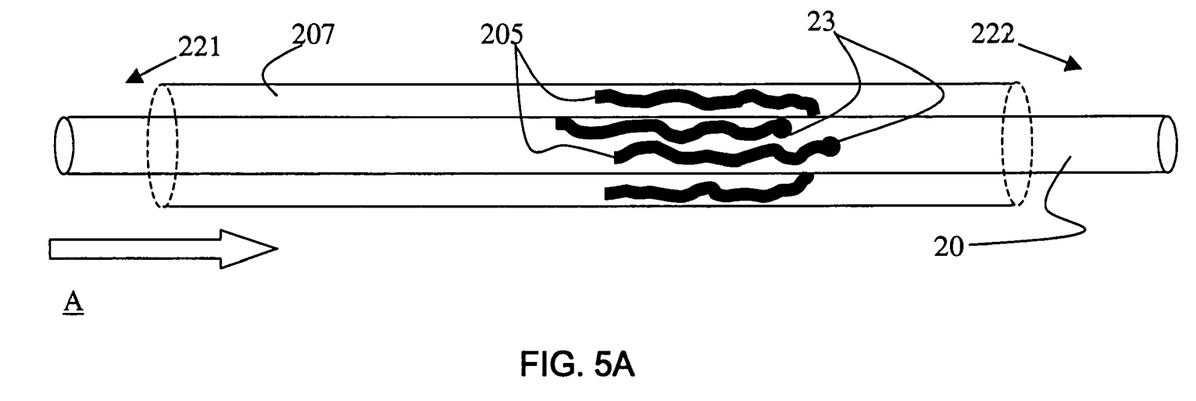
FIGS. 5A–B are schematic views of a portion of a lead body including retention means according to yet another embodiment of the present invention.
Figure 5B:
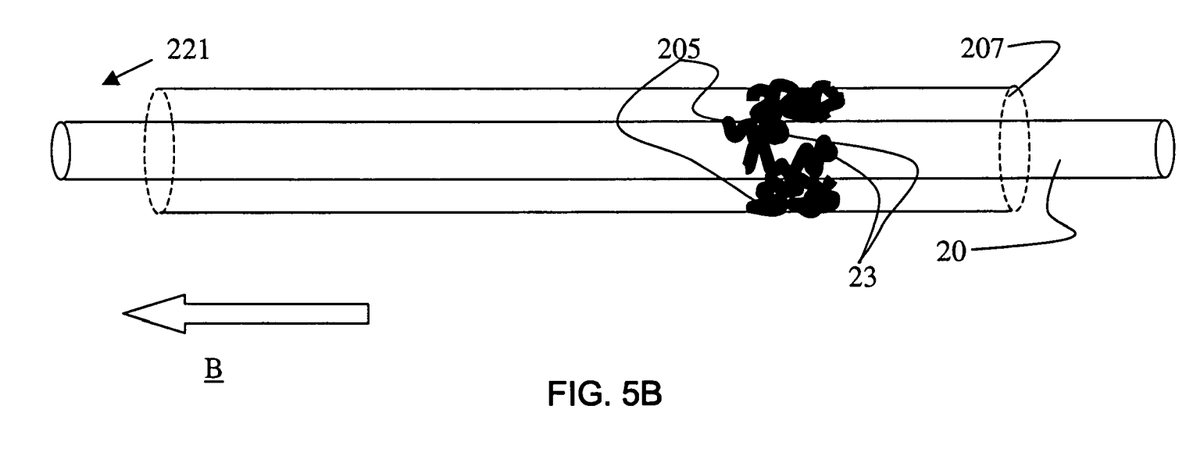

FIGS. 5A–B schematic views of a portion of a lead body including retention means according to yet another embodiment. FIGS. 5A–B illustrate a lead body 20 including a plurality of hair-like projections or fibers 205 each attached at one end to lead body 20 and directed by their attachment points 23 to extend out from and along a length of body 20 toward a proximal end 221 of body 20. According to the illustrated embodiment, as lead body 20 is advanced distally in a vessel 207 per arrow A, as in FIG. 5A, projections 205 are suspended proximally; when lead body 20 is retracted proximally per arrow B, as in FIG. 5B, projections 205 are forced toward a distal end 222 of body 20 to become bunched up and wedged between body 20 and a wall of vessel 207, thereby providing retention means for lead body 20. Projections may be formed from a bioadsorbable polymer, for example polyglyocolic acid or polylactic acid. Alternately projections 205 may be formed from polyester fibers or some other material promoting thrombotic adhesion with the vessel wall to enhance retention within vessel 207; such thrombotic projections may include a non-thrombogenic coating adapted to dissolve after the lead is positioned per FIG. 5B, examples of which include a benzalkonium chloride-heparin solution and polyvinylpyrrolidone. Projections 205 may be attached at attachment points 23 by embedment within lead body 20 or by adhesive attachment, for example by means of silicone medical adhesive.

FIG. 6 is a schematic view of an exemplary medical device, which may incorporate retention means according to embodiments of the present invention. FIG. 6 illustrates the medical device including a therapy generator 600 coupled to a lead 60 implanted within branch vessel 607 emanating from coronary sinus 605. Lead 60 including a connector terminating a proximal portion 62, an electrode in proximity to a distal end 66 and a conductor extending through an outer insulative sheath (similar to lead 10 illustrated in FIG. 1) may deliver electrical therapy, or may deliver infusions of therapeutic fluids from generator 600 through a central lumen. FIG. 6 further illustrates potential retention segment sites 65, 61, and 63 along lead 60 where projections of retention segments according to embodiments of the present invention would engage a wall of vessels 605 and 607 to prevent rearward dislodgment of lead 60 from vessel 607.

Although embodiments of the present invention are described in the context of therapy delivery, diagnostic devices adapted for insertion within a blood vessel may also incorporate retention means described herein and thus fall within the scope of the present invention. In the foregoing detailed description, the invention has been described with reference to specific embodiments. However, it may be appreciated that various modifications and changes can be made without departing from the scope of the invention as set forth in the appended claims.

What is claimed is:

1. A medical device, comprising:
   an elongate body comprising a proximal end, a distal end, an outer sheath, and a conductor extending within the sheath and between the proximal and distal ends of the body;
   the sheath having an overall length and including a retaining segment extending along a length, which is less than the overall length; the retaining segment forming a fixed portion of an outer surface of the sheath and including a plurality of projections extending from the portion of the outer surface;
   wherein the plurality of projections are adapted to interfere with a wall of a generally tubular vessel to retain the body within the vessel; and
   the plurality of projections lie approximately parallel with the portion of the outer surface when the length is approximately straight and protrude laterally from the portion of the outer surface when the length is bent.

2. The device of claim 1, wherein the length is positioned in proximity to the distal end of the body.

3. The device of claim 1, wherein the length is positioned in proximity to the proximal end of the body.

4. The device of claim 1, wherein the retaining segment extends about an entire circumference of the sheath.

5. The device of claim 1, wherein the retaining segment extends about a portion of a circumference of the sheath.

6. The device of claim 1, further comprising a dissolvable coating temporarily covering the plurality of projections.

7. The device of claim 1, further comprising a thin walled tube-covering deployable over the plurality of projections.

8. The device of claim 1, wherein the body includes at least one preformed curve in proximity to the retaining segment.

9. The device of claim 8, wherein the at least one preformed curve includes a first curve positioned proximal to the retaining segment and a second curve positioned distal to the retaining segment.

10. The device of claim 8, wherein the at least one preformed curve includes a curve positioned proximal to the retaining segment.

11. The device of claim 8, wherein the at least one preformed curve includes a curve positioned distal to the retaining segment.

12. The device of claim 8, wherein the one or more preformed curves include a curve positioned along the length over which the retaining segment extends.

13. The device of claim 1, wherein each of the plurality projections have a length greater than approximately 100 microns.

14. The device of claim 13, wherein the projection length is between approximately 100 microns and approximately 1 mm.

15. The device of claim 13, wherein the projection length is greater than approximately 1 mm.

16. The device of claim 1, wherein the length of the body over which the retaining segment extends is greater than or equal to approximately 1 mm.

17. The device of claim 16, wherein the length is greater than approximately 5 mm.

18. The device of claim 1, wherein a plasma deposition process forms the plurality of projections.

19. The device of claim 1, wherein a molding process forms the plurality of projections.

20. The device of claim 1, wherein an extrusion process forms the plurality of projections.

21. The device of claim 1, wherein a cutting process forms the plurality of projections.

22. The device of claim 1, wherein a laser ablation process forms the plurality of projections.

23. The device of claim 1, wherein the projections are included in a coating adhered to the retaining segment.

24. The device of claim 1, wherein the plurality of projections are fish scale-like.

25. A medical device, comprising:
an elongate body comprising a proximal end, a distal end and a sheath having a length extending between the proximal and distal ends; and
a collar positioned about the body and having a length less than the sheath length, the collar forming a fixed portion of an outer surface of the body and including a plurality of projections extending from the portion of the outer surface;
wherein the plurality of projections are adapted to interfere with a wall of a generally tubular vessel to retain the body within the vessel; and
the plurality of projections lie approximately parallel with the portion of the outer surface when the length of the collar is approximately straight, and protrude laterally from the outer surface when the length of the collar is bent.

26. The device of claim 25, wherein the collar is formed from a bioabsorbable material.

27. The device of claim 25, wherein the collar is formed of a material comprising silicone.

28. The device of claim 25, wherein the collar is formed of a material comprising polyurethane.

29. A medical device, comprising:
an elongate body; and
a retaining segment extending along a length of the body and forming a fixed portion of an outer surface of the body;
the retaining segment comprising a first material and a plurality of projections, each of the plurality of projections being formed from a second material separate from the first material, and the projections extending from the fixed portion of the outer surface;
wherein the projections are embedded in the first material of the retaining segment;
the second material forming each projection is selected from the group consisting of metal particles, hard plastic particles, carbon particles, polymer fibers, and carbon fibers; and
the projections are adapted to interfere with a wall of a generally tubular vessel to retain the body within the vessel.

30. The device of claim 29, wherein the retaining segment further includes a proximal end and each of the plurality of projections includes a terminal edge directed toward the proximal end of the retaining segment.

31. The device of claim 29, further comprising a dissolvable coating temporarily covering the plurality of projections.

32. The device of claim 29, further comprising a thin walled tube-covering deployable over the plurality of projections.

33. The device of claim 29, wherein the body includes at least one preformed curve in proximity to the retention segment.

34. The device of claim 33, wherein the at least one preformed curve includes a first curve positioned proximal to the retaining segment and a second curve positioned distal to the retaining segment.

35. The device of claim 33, wherein the at least one preformed curve includes a curve positioned proximal to the retaining segment.

36. The device of claim 33, wherein the at least one preformed curve includes a curve positioned distal to the retaining segment.

37. The device of claim 33, wherein the one or more preformed curves include a curve positioned along the length of the body over which the retaining segment extends.

38. A medical device, comprising:
an elongate body; and
a retaining segment extending along a length of the body and forming a fixed portion of an outer surface of the body, the retaining segment including a plurality of projections extending from the portion of the outer surface;
wherein the plurality of projections are adapted to interfere with a wall of a generally tubular vessel in order to retain the body within the vessel; and
one or more of the plurality of projections include microfeatures positioned along the length of the projection for interfacing with the vessel wall, when the projections interfere with the wall, in order to enhance engagement of the one or more projections with the vessel wall.

* * * * *